United States Patent [19]

Matsuoka et al.

[11] Patent Number: 5,202,354
[45] Date of Patent: Apr. 13, 1993

[54] COMPOSITION AND METHOD FOR REDUCING ACETALDEHYDE TOXICITY

[75] Inventors: Masayoshi Matsuoka, Habikino; Go Kito, Yao, both of Japan

[73] Assignee: Takeda Chemical Industries, Ltd., Osaka, Japan

[21] Appl. No.: 839,265

[22] Filed: Feb. 21, 1992

Related U.S. Application Data

[63] Continuation of Ser. No. 13,443, Feb. 10, 1987, abandoned.

[30] Foreign Application Priority Data

Feb. 18, 1986 [JP] Japan .................................. 61-34494

[51] Int. Cl.$^5$ ................... A01N 37/00; A01N 43/08
[52] U.S. Cl. ................................ 514/562; 514/474; 514/811
[58] Field of Search ................ 514/557, 562, 474, 811

[56] References Cited

U.S. PATENT DOCUMENTS

| | | | |
|---|---|---|---|
| 2,283,817 | 5/1942 | Martin et al. | 514/562 X |
| 4,496,548 | 1/1985 | Moldowan et al. | 514/27 |
| 4,528,295 | 7/1985 | Tabakoff | 514/562 X |
| 4,593,020 | 6/1986 | Guinot | 514/811 |

OTHER PUBLICATIONS

Sprince et al., Agents and Actions, vol. 5/2 (1975), pp. 164–173.

*Primary Examiner*—Arthur C. Prescott
*Attorney, Agent, or Firm*—Wenderoth, Lind & Ponack

[57] ABSTRACT

A novel composition and method are disclosed for reducing acetaldehyde toxicity, especially for preventing and relieving hangover symptoms in humans. The composition comprises (a) a compound of the formula:

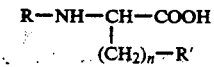

wherein R is hydrogen or an acyl group; R' is thiol or sulfonic group; and n is an integer of 1 or 2, (b) ascorbic acid or a salt thereof and (c) a disulfide type thiamine derivative or a salt thereof. The composition is orally administered, preferably in the form of tablets.

7 Claims, No Drawings

COMPOSITION AND METHOD FOR REDUCING ACETALDEHYDE TOXICITY

This application is a continuation of now abandoned application Ser. No. 07/013,443 filed Feb. 10, 1987 now abandoned.

The present invention relates to a composition and method for reducing acetaldehyde toxicity, especially for preventing and relieving katzenjammer.

Katzenjammer or hangover which occurs on drinking, particularly on excessive drinking, is characterized by various manifestations such as skin flushes, hot sensation, chest distress, headache, dull headache, nausea, vomiting, breath odor, urinous odor, and so on, and at times is accompanied by cerebral edema, functional neuritis and other symptoms.

Currently, against such symptoms as heaviness in the stomach, nausea, heart-burn, etc., various gastrointestinal remedies, crude drugs, etc. are generally ingested in hopes of relieving the uncomfortable symptoms.

It is generally acknowledged that a hangover is mainly caused by unmetabolized residues of acetaldehyde, which is a metabolic intermediate of alcohol, in the drinker's body. Therefore, it has been thought that reducing the blood level of acetaldehyde should help prevent and treat hangover symptoms, and further, contribute to the prevention and treatment of liver damage associated with acetaldehyde.

For example, Herbert Sprince et al. studied the antagonistic effects of various drugs against the anesthetic and lethal effects of acetaldehyde in animals and reported that a combination of L-ascorbic acid, L-cysteine, and thiamine hydrochloride exhibits an excellent antagonizing effect against acetaldehyde toxicity. [Agents and Actions, Vol. 5/2, pp. 164–173 (1975)]. Today, in view of the high frequency of drinking in daily life and the increasing consumption of alcohol, a need has been keenly felt for the development of an etiotropically effective medication for the prevention and treatment of hangover symptoms apparently associated with the toxic action of acetaldehyde.

The present inventors found surprisingly that the addition of fursultiamine (TTFD), which is in common use as the so-called activated vitamin $B_1$, to a basal mixture of L-cysteine and L-ascorbic acid results in a remarkably greater acetaldehyde-antagonizing effect as compared with the conventional ternary mixture of L-cysteine, L-ascorbic acid and thiamine hydrochloride. It was also found that the formulation containing activated vitamin $B_1$ increases mitocondrial acetaldehyde dehydrogenase activity in rats. Further, the present inventors found that the addition of ursodesoxycholic acid, a cholagogue, to the above formula of L-cysteine, L-ascorbic acid and fursultiamine results in a further potentiated antagonism against the anesthetic and lethal effects of acetaldehyde.

The present invention is the result of further investigations based on the above findings.

The present invention is therefore directed to a composition for reducing acetaldehyde toxicity comprising, as combined active components, an effective amount of (a) a compound of the formula:

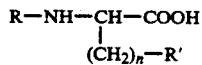

(I)

wherein R is hydrogen or an acyl group; R' is thiol or sulfonic (sulfo) group; and n is an integer of 1 or 2, (b) ascorbic acid or a salt thereof and (c) a disulfide type thiamine derivative or a salt thereof, and to a method for reducing acetaldehyde toxicity which comprises administering to human subjects, before and/or after drinking, an effective amount of a composition comprising the components as defined above.

Referring to the above general formula (I), the acyl group denoted by R is exemplified by lower alkyl ($C_{1-4}$)carbonyl groups such as acetyl, propionyl and so on. In the present invention, the L-form compound (I) is preferably employed but the racemic compound may also be used. Examples of (I) include L-cysteine, N-acetyl-L-cysteine, L-homocysteine, L-cysteic acid and L-homocysteic acid and the corresponding racemates. Moreover, the compound (I) may be a mineral acid salt such as L-cysteine hydrochloride or an alkali metal salt such as sodium L-cysteinate. Preferred is L-cysteine.

The ascorbic acid mentioned above may be L-ascorbic acid. The salt of ascorbic acid includes such physiologically acceptable salts as the alkali metal and alkaline earth metal salts, for example, the sodium salt, calcium salt and so on.

The disulfide type thiamine derivative may be any of the known active vitamin $B_1$ compounds having the S—S linkage in the molecule. For example, the following compounds may be mentioned. (i) Thiamine disulfide and its derivatives, such as thiamine disulfide (TDS), bisbentiamine (BTDS), bisbutitiamine (BuTDS), bisibutiamine and so on. (ii) Thiamine alkyl disulfide derivatives, such as prosultiamine (TPD), fursultiamine (TTFD), octotiamine (TATD) and so on.

In the present invention, said thiamine compound may be used either in its free form or as a physiologically acceptable salt such as hydrochloride, nitrate and other mineral acid salts. It should be understood that since the thiamine compound may interact with said compound (I), the formulation is made so as to avoid direct contact of the two compounds.

In a further aspect of the present invention, a cholagogue is added to the above 3-component formulation to provide a product having a still improved acetaldehyde-detoxicating effect.

The cholagogue is exemplified by ursodesoxycholic acid, dehydrocholic acid, osalmid(hydroxyphenyl salicylamide), phenylpropanol, anethole trithione, cyclobutyrol calcium, cyclobutyrol, hymecromone, trepibutone, chenodeoxycholic acid, etc. but is not limited to those mentioned. Thus, any component having hepatic circulation increasing activity or liver function improving activity can be employed. In the practice of the present invention, the use of cholic acid derivatives having steroid nuclei, particularly ursodesoxycholic acid, is preferred.

The position having acetaldehyde-detoxicating effect of the present invention is not limited to a composition consisting of the above-mentioned three components or four components. If necessary, various vitamins and the like, such as calcium pantothenate, nicotinamide, riboflavine, tocopherol acetate, etc., may be added to the composition.

The composition according to the present invention can be orally administered to human subjects. As to dosage forms, tablets, granules, capsules and other optional forms can be provided. For the manufacture of such preparations, the established pharmaceutical procedures such as sugar coating, granulation, etc. can be employed. Thus, solid preparations may be produced using excipients such as lactose, starch, crystalline cellulose, potassium hydrogen phosphate, etc., lubricants such as magnesium stearate, talc, etc., and binders such as starch, polyvinylpyrrolidone, methylcellulose, hydroxypropylcellulose, and so on. In the case of a preparation containing the compound (I) and a pharmaceutically active substance which would interact therewith, such as a disulfide type thiamine derivative, a sugar-coated tablet containing one of the components in the plain tablet core and the other in the sugar coat may be provided. Alternative methods include the method which comprises granulating these components into independent granules and blending them, the method which comprises coating some of the granules and tableting them with the remaining granules, and the nucleation tableting method in which the two components are formed into the core and the outer layer, respectively.

The dosage of each component may be selected generally from the following ranges.

(a) Compound (I)
About 150 to 300 mg/day (about 150 to 300 parts by weight)

(b) Ascorbic acid or a salt thereof (as free ascorbic acid)
About 250 to 2000 mg/day (about 250 to 2000 p by weight)

(c) A disulfide type thiamine derivative or a salt thereof (as free compound)
About 20 to 100 mg/day (about 20 to 100 parts by weight)

(d) A cholagogue
About 20 to 150 mg/day (about 20 to 150 parts by weight)

The above daily dose is administered before and/or after drinking, or preferably before and after drinking in two divided doses.

The composition according to the present invention has activity to effectively lower the blood concentration of acetaldehyde. Therefore, it is of considerable value as a therapeutic and prophylactic composition for katzenjammer associated with drinking, or further as an acetaldehyde-detoxicating agent. The composition has remarkably low acute toxicity ($LD_{50}$ orally in rats: >5000mg/kg).

EXPERIMENTAL EXAMPLE I

Rats (body weights 250–280 g) fasted for 18 hours were previously dosed orally with each of test compositions Formula A to Formula G as shown in below. Control group received a corresponding volume of saline by the same route. After a predetermined time (45–60 min ), acetaldehyde (1370 mg/kg) was orally administered to the rats and the effect of Formula A to Formula G on the anesthetic and lethal effects of acetaldehyde was observed.

When 1370 mg/kg of acetaldehyde was administered without prior treatment with the test compositions, the rats (control group) fell into anesthesia within several minutes, and then developed dyspnea and the like and 90% of them died within 1 to 6 hours.

| Formula | Components | Dosage (mg/kg) |
|---|---|---|
| A | Fursultiamine hydrochloride | 100 |
|   | L-Ascorbic acid | 352 |

-continued

| Formula | Components | Dosage (mg/kg) |
|---|---|---|
|   | L-Cysteine | 169 |
| B | Thiamine hydrochloride | 100 |
|   | L-Ascorbic acid | 352 |
|   | L-Cysteine | 169 |
| C | L-Ascorbic acid | 352 |
|   | L-Cysteine | 169 |
| D | Fursultiamine hydrochloride | 50 |
|   | L-Ascorbic acid | 352 |
|   | L-Cysteine | 169 |
| E | Fursultiamine hydrochloride | 20 |
|   | L-Ascorbic acid | 352 |
|   | L-Cysteine | 169 |
| F | Fursultiamine hydrochloride | 50 |
|   | Ursodesoxycholic acid | 30 |
|   | L-Ascorbic acid | 352 |
|   | L-Cysteine | 169 |
| G | Fursultiamine hydrochloride | 20 |
|   | Ursodesoxycholic acid | 30 |
|   | L-Ascorbic acid | 352 |
|   | L-Cysteine | 169 |

Note:
Formulas B and C are a formulation for comparision.

(1) The results with Formula A, B and C are shown in Table 1.

TABLE 1

Antagonistic Effects of Formula A, B and C on the anesthetic and lethal effects of acetaldehyde

| Formula | Anesthesia (%) | Mortality (%) After 1 hr | After 6 hr |
|---|---|---|---|
| Control | 81.2 (69/85) | 89.4 (76/85) | 90.6 (77/85) |
| A | 35.2 (19/54) | 33.3 (18/54) | 35.2 (19/54) |
| B | 60.0 (21/35) | 62.9 (22/35) | 71.4 (25/35) |
| C | 74.3 (26/35) | 60.0 (21/35) | 74.3 (26/35) |

( ): responsive cases/cases used

It will be apparent from Table 1 that whereas Formula C consisting of L-cysteine and L-ascorbic acid and Formula B consisting of Formula C plus thiamine hydrochloride are equivalent in effect, with the mortality due to acetaldehyde being approximately 70%, Formula A consisting of C plus fursultiamine showed a significantly superior antagonizing effect with a mortality of 35%.

The above results indicate that fursultiamine hydrochloride is more effective than thiamine hydrochloride.

(2) The results with Formulas D and E are shown in Table 2.

TABLE 2

Antagonistic Effects of Formula D and E on the anesthetic and lethal effects of acetaldehyde

| Formula | Anesthesia (%) | Mortality (%) After 1 hr | After 6 hr |
|---|---|---|---|
| Control | 83.2 (79/85) | 90.5 (86/95) | 91.5 (87/95) |
| D | 40.0 (8/20) | 30.0 (6/20) | 35.0 (7/20) |
| E | 60.0 (12/20) | 45.0 (9/20) | 45.0 (9/20) |

( ): responsive cases/cases used

In view of the confirmed effectiveness of fursultiamine hydrochloride in the above investigation (1), a dosage-finding study was conducted. It will be apparent from Table 2 that Formula D containing 50 mg/kg was as effective as Formula A containing 100 mg/kg and that even Formula E containing only 20 mg/kg showed a satisfactory result with a mortality of 45%. It is, therefore, considered that the use of fursultiamine hydrochloride is fully effective at the level of addition of 20 mg/kg.

(3) The results with Formulas F and G are shown in Table 3.

TABLE 3

Antagonistic Effects of Formula F and G on the anesthetic and lethal effects of acetaldehyde

| Formula | Anesthesia (%) | Mortality (%) After 1 hr | After 6 hr |
|---------|----------------|--------------------------|------------|
| Control | 84.8 (89/105) | 90.4 (95/105) | 91.4 (96/105) |
| F | 32.0 (8/25) | 28.0 (7/25) | 28.0 (7/25) |
| G | 32.0 (8/25) | 32.0 (8/25) | 40.0 (10/25) |

( ): responsive cases/cases used

The effect of addition of the cholagogue ursodesoxycholic acid to Formulas D and E was investigated. It will be apparent from Table 3 that Formulas F and G each supplemented with 30 mg/kg of ursodesoxycholic acid showed results more favorable than Formulas D and E.

(4) As a conclusion, a ternary composition of L-cysteine, L-ascorbic acid and fursultiamine hydrochloride antagonized the anesthetic and lethal effects of acetaldehyde. It was further found that the addition of ursodesoxycholic acid, producing an increase in hepatic blood flow and an improvement in liver function, to the above ternary composition results in a further potent antagonistic effect.

The fact that the excellent antagonistic action of the present drug on the anesthetic and lethal effects of acetaldehyde was thus demonstrated in animal experiments suggest the likelihood that the drug is also effective in the prevention and treatment of hangover symptoms in man wherein acetaldehyde is primarily involved.

EXPERIMENTAL EXAMPLE II

The same experiment as Experimental Example I was carried out with each of test compositions Formula H and I and the results obtained are shown in Table 4.

| Formula | Components | Dosage (mg/kg) |
|---------|-----------|----------------|
| H | bisibutiamine | 50 |
| | L-ascorbic acid | 352 |
| | L-cysteine | 169 |
| I | bisbentiamine (BTDS) | 50 |
| | L-ascorbic acid | 352 |
| | L-cysteine | 169 |

TABLE 4

Antagonistic Effects of Formula H and I on the anesthetic and lethal effects of acetaldehyde

| Formula | Anesthesia (%) | Mortality (%) After 1 hr | After 6 Hr |
|---------|----------------|--------------------------|------------|
| Control | 100 (30/30) | 100 (30/30) | 100 (30/30) |
| H | 40.0 (12/30) | 33.3 (10/30) | 46.7 (14/30) |
| I | 43.3 (13/30) | 43.3 (13/30) | 50.0 (15/30) |

( ): responsive cases/cases used

EXPERIMENTAL EXAMPLE III

Sugar-coated tablets prepared according to the undermentioned formula were administered orally to human subjects for a clinicopharmacological study (hereinafter referred to briefly as the drinking test) using the blood ethanol and acetaldehyde concentrations and the time course of hangover symptoms after alcohol loading as indicators.

| Formula | Amount |
|---------|--------|
| L-Cysteine | 240 mg |
| L-Ascorbic acid | 500 mg |
| Fursultiamine | 25 mg |
| Ursodesoxycholic acid | 30 mg |
| | (in 6 tablets) |

(1) Healthy volunteers which had abstained from drinking for 24 hours prior to the study were instructed to drink 2 g/kg of alcohol whisky diluted with carbonated water) in about an hour and the subsequent course of blood ethanol and acetaldehyde concentrations was investigated. The time course of hangover symptoms (hot flushes, heat sensation, chest distress, headache, dull headache, nausea, etc.) was also monitored.

For an objective assessment of effects, the study was conducted in a single blind cross-over design using the active drug and its placebo.

The drug was administered (3 tablets per dose) in 2 doses, one hour before initiation of drinking and two hours after initiation of drinking. The results are given in Table 5

It will be apparent from Table 5 that whereas no difference was found between active drug and placebo in blood ethanol concentration, the blood acetaldehyde level showed an overt decrease with the active drug as compared to the placebo. In correspondence with the decrease in blood acetaldehyde concentration, such hangover symptoms as hot flushes, heat sensation, chest distress, headache, dull headache, nausea, breath odor based probably on aldol component and urinous odor were also abated.

TABLE 5

Drinking Test

| Time after initiation of drinking (min.) | Parameter | $CH_3CHO$ ($\mu M/l$) | $C_2H_5OH$ ($mM/l$) | $CH_3CHO$ ($\mu M/l$) | $C_2H_5OH$ ($mM/l$) |
|---|---|---|---|---|---|
| Subject | | 52-year-old male (M.M) | | 48-year-old male (F.N) | |
| 60 | Place- | 4.28 | 43.82 | 4.80 | 36.82 |
| 240 | bo | 4.35 | 32.82 | 4.09 | 18.88 |
| 300 | | 3.13 | 31.60 | 4.03 | 17.91 |
| 60 | Active | 2.75 | 46.77 | 2.62 | 39.20 |
| 240 | drug | 3.07 | 32.60 | 1.79 | 29.08 |
| 300 | | 2.88 | 29.52 | 2.68 | 29.14 |
| Subject | | 35-year-old male (K.Y) | | 24-year-old male (T.Y) | |
| 60 | Place- | 7.91 | 34.60 | 5.95 | 22.28 |
| 240 | bo | 4.53 | 24.76 | 5.17 | 23.52 |
| 300 | | 4.66 | 22.40 | 6.81 | 23.31 |
| 60 | Active | 4.72 | 33.50 | 3.36 | 12.52 |
| 240 | drug | 3.89 | 23.60 | 4.68 | 20.55 |
| 300 | | 3.95 | 19.08 | 5.86 | 15.10 |
| Subject | | 24-year-old male (H.T) | | 30-year-old male (T.F) | |
| 60 | Place- | 4.31 | 23.60 | 16.17 | 18.68 |
| 240 | bo | 3.76 | 28.51 | 36.22 | 27.71 |
| 300 | | 3.45 | 19.57 | 19.19 | 23.61 |
| 60 | Active | 3.36 | 15.22 | 12.02 | 14.70 |
| 240 | drug | 2.80 | 21.56 | 7.99 | 52.95 |
| 300 | | 6.14 | 35.57 | 7.32 | 33.75 |
| Subject | | 35-year-old male (T.A) | | | |
| 60 | Place- | 33.42 | 24.75 | | |

TABLE 5-continued

Drinking Test

| Time after initiation of drinking (min.) | Parameter | CH₃CHO (μM/l) | C₂H₅OH (mM/l) | CH₃CHO (μM/l) | C₂H₅OH (mM/l) |
|---|---|---|---|---|---|
| 240 | bo | 8.30 | 32.65 | | |
| 300 | | 21.43 | 36.77 | | |
| 60 | Active | 20.93 | 38.47 | | |
| 240 | drug | 7.60 | 37.52 | | |
| 300 | | 9.48 | 42.51 | | |

The above Experimental Examples I, II and III revealed the following. The formulation consisting of L-cysteine, L-ascorbic acid, fursultiamine hydrochloride and ursodesoxycholic acid has proved to have detoxicating effects against the toxicity of acetaldehyde which is said to be a primary cause of hangover symptoms in animal experiments. Further, in the clinicopharmacological study in healthy volunteers, the above formulation promoted clearance of blood acetaldehyde to thereby display prophylactic and therapeutic effects against hangover symptoms.

EXAMPLE 1

By means of a compression tableting machine, plain tablets were first prepared using the following ingredients in the following amounts per 6 tablets.

| Ascorbic acid | 500 mg |
|---|---|
| L-Cysteine | 240 mg |
| Starch | 280 mg |
| Lactose | 500 mg |
| Magnesium stearate | 10 mg |

Then, in a coating pan, the plain tablets were sugar-coated with a syrup and a spray composition containing 25 mg (per 6 tablets; the same applies hereinafter) of fursultiamine hydrochloride to give sugar-coated tablets.

EXAMPLE 2

By means of a compression tableting machine, plain tablets were first prepared using the following ingredients in the following amounts per 6 tablets. Then, in a coating pan, the plain tablets were sugarcoated with a syrup and a spray composition containing 50 mg of fursultiamine hydrochloride to give sugar-coated tablets.

| Ascorbic acid | 500 mg |
|---|---|
| L-Cysteine | 240 mg |
| Starch | 250 mg |
| Lactose | 500 mg |
| Magnesium stearate | 10 mg |

Then, in a coating pan, the plain tablets were sugarcoated with a syrup and a spray composition containing 50 mg of fursultiamine hydrochloride to give sugar-coated tablets.

EXAMPLE 3

By means of a compression tableting machine, plain tablets were prepared using the following ingredients in the following amounts per 6 tablets.

| Ascorbic acid | 250 mg |
|---|---|
| L-Cysteine | 240 mg |
| Starch | 530 mg |
| Lactose | 500 mg |
| Magnesium stearate | 10 mg |

In a coating pan, the above plain tablets were coated with a syrup and a spray composition containing 25 mg of fursultiamine hydrochloride to give sugar-coated tablets.

EXAMPLE 4

By means of a compression tableting machine, plain tablets were first prepared using the following ingredients in the following amounts per 6 tablets.

| Ascorbic acid | 500 mg |
|---|---|
| L-Cysteine | 240 mg |
| Ursodesoxycholic acid | 30 mg |
| Starch | 250 mg |
| Lactose | 500 mg |
| Magnesium stearate | 10 mg |

In a coating pan, these plain tablets were coated with a syrup and a spray composition containing 25 mg of fursultiamine hydrochloride to give sugar-coated tablets.

EXAMPLE 5

By means of a compression tableting machine, plain tablets were first prepared using the following ingredients in the following amounts per 6 tablets.

| Ascorbic acid | 500 mg |
|---|---|
| L-Cysteine | 240 mg |
| Ursodesoxycholic acid | 30 mg |
| Starch | 240 mg |
| Lactose | 500 mg |
| Magnesium stearate | 10 mg |

In a coating pan, these plain tablets were coated with a syrup and a spray composition containing 34.3 mg of fursultiamine hydrochloride to give sugar-coated tablets.

What is claimed is:

1. A composition for reducing acetaldehyde toxicity associated with drinking alcohol which comprises, as combined active components, an effective amount of
   (a) a compound of the formula:

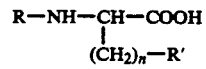

wherein R is hydrogen or an alkylcarbonyl group having 1-4 carbon atoms in the alkyl moiety; R' is a thiol or sulfonic group; and n is an integer of 1 or 2,
   (b) ascorbic acid or a physiologically acceptable salt thereof, and
   (c) a member selected from the group consisting of thiamine disulfide, bisbentiamine, bisbutitiamine, bisibutiamine, prosultiamine, fursultiamine, octotiamine and a physiologically acceptable salt thereof.

2. The composition of claim 1, wherein the composition further comprises (d) a chalagogue.

3. The composition of claim 1, wherein the component (a) is in an amount of about 150 to 300 parts by weight, the component (b) is in an amount of about 250 to 2000 parts by weight and the component (c) is in an amount of about 20 to 100 parts by weight.

4. The composition of claim 2, wherein the component (a) is in an amount of about 150 to 300 parts by weight, the component (b) is in an amount of about 250 to 2000 parts by weight, the component (c) is in an amount of about 20 to 100 parts by weight and the component (d) is in an amount of about 20 to 150 parts by weight.

5. A method for reducing acetaldehyde toxicity, which comprises administering to human subjects, before and/or after drinking alcohol, an effective amount of a composition comprising:

(a) a compound of the formula:

$$R-NH-CH(-(CH_2)_n-R')-COOH$$

wherein R is hydrogen or an alkylcarbonyl group having 1-4 carbon atoms in the alkyl moiety; R' is a thiol or sulfonic group; and n is an integer of 1 or 2, (b) ascorbic acid or a physiologically acceptable salt thereof, and (c) a member selected from the group consisting of thiamine disulfide, bixbentiamine, bisbutitiamine, bisibutiamine, prosultiamine, fursultiamine, octotiamine and a physiologically acceptable salt thereof.

6. The method of claim 5, wherein the composition is orally administered in a pharmaceutically effective dose before and/or after drinking alcohol.

7. A composition for inhibiting or relieving hangover symptoms resulting from drinking alcohol, which comprises, as combined active components, an effective amount of (a) a compound of the formula:

$$R-NH-CH(-(CH_2)_n-R')-COOH$$

wherein R is hydrogen or an alkylcarbonyl group having 1-4 carbon atoms in the alkyl moiety; R' is a thiol or sulfonic group; and n is an integer of 1 or 2, (b) ascorbic acid or a physiologically acceptable salt thereof, and (c) a member selected from the group consisting of thiamine disulfide, bisbentiamine, bisbutitiamine, bisibutiamine, prosultiamine, fursultiamine, octotiamine and a physiologically acceptable salt thereof.

* * * * *

UNITED STATES PATENT AND TRADEMARK OFFICE
CERTIFICATE OF CORRECTION

PATENT NO.   : 5,202,354
DATED        : April 13, 1993
INVENTOR(S)  : Masayoshi MATSUOKA et al.

It is certified that error appears in the above-indentified patent and that said Letters Patent is hereby corrected as shown below:

Column 8, last line, change "chalagogue" to --cholagogue--.

Column 10, line 2, change "bixbentiamine" to --bisbentiamine--.

Signed and Sealed this

Fourteenth Day of December, 1993

Attest:

BRUCE LEHMAN

*Attesting Officer*   *Commissioner of Patents and Trademarks*